United States Patent
Howell

(10) Patent No.: US 10,632,267 B2
(45) Date of Patent: Apr. 28, 2020

(54) INHALER HOUSING

(71) Applicant: MIRROR 5 LTD, West Kirby (GB)

(72) Inventor: Michael Howell, West Kirby (GB)

(73) Assignee: MIRROR 5 LTD, West Kirby (GB)

(*) Notice: Subject to any disclaimer, the term of this patent is extended or adjusted under 35 U.S.C. 154(b) by 0 days.

(21) Appl. No.: 15/781,414

(22) PCT Filed: Nov. 30, 2016

(86) PCT No.: PCT/GB2016/053748
§ 371 (c)(1),
(2) Date: Jun. 4, 2018

(87) PCT Pub. No.: WO2017/093721
PCT Pub. Date: Jun. 8, 2017

(65) Prior Publication Data
US 2018/0361087 A1 Dec. 20, 2018

(30) Foreign Application Priority Data

Dec. 2, 2015 (GB) .................................. 1521241.8

(51) Int. Cl.
*A61M 15/00* (2006.01)
(52) U.S. Cl.
CPC ...... *A61M 15/0023* (2014.02); *A61M 15/009* (2013.01); *A61M 15/0021* (2014.02); *A61M 2205/0216* (2013.01)
(58) Field of Classification Search
CPC ............... A61M 15/00; A61M 15/009; A61M 15/0001; A61M 15/06;
(Continued)

(56) References Cited

U.S. PATENT DOCUMENTS 3,506,004 A 4/1970 Mann et al.
3,610,480 A 10/1971 Lipfert
(Continued)

FOREIGN PATENT DOCUMENTS

DE 3911985 C1 4/1989
GB 1333438 10/1973
(Continued)

OTHER PUBLICATIONS

Invitation to Pay Additional Fees and, Where Applicable, Protest Fee mailed Feb. 28, 2017 for International Application No. PCT/GB2016/053748.

*Primary Examiner* — Colin W Stuart
*Assistant Examiner* — Matthew D Ziegler
(74) *Attorney, Agent, or Firm* — Womble Bond Dickinson (US) LLP; Daniel E. Ovanezian

(57) ABSTRACT

An inhaler housing is described having a body for receiving an inhaler canister and a mouthpiece through which a dose from the inhaler canister is to be delivered. The body and the mouthpiece are rotatably coupled so that by turning the mouthpiece relative to the body the inhaler housing is converted between a carry configuration in which the mouthpiece and body are mutually aligned, and a use configuration in which the mouthpiece projects laterally from the body. The inhaler housing has a member which is variably elastically deformed as the mouthpiece is turned, investing the member with elastic potential energy minima corresponding to the carry configuration and the use configuration. Rotation of the mouthpiece relative to the body tends to stop when either of these configurations is reached.

12 Claims, 7 Drawing Sheets

(58) Field of Classification Search
CPC .......... A61M 15/0021–0026; A61M 15/0086; A61M 15/0088; A61M 15/0065–0083; A61M 2202/0007; A61M 2205/27; A61M 2205/276; A61M 2205/58; A61M 2205/582; A61M 2205/583; A61M 2210/0625
See application file for complete search history.

(56) References Cited

U.S. PATENT DOCUMENTS

| | | | |
|---|---|---|---|
| 4,637,528 A | 1/1987 | Wachinski et al. | |
| 4,641,644 A | 2/1987 | Andersson et al. | |
| 5,755,218 A * | 5/1998 | Johansson | A61M 15/00 128/200.14 |
| 5,904,139 A | 5/1999 | Hauser | |
| 6,182,655 B1 * | 2/2001 | Keller | A61M 15/0045 128/203.12 |
| 6,293,279 B1 * | 9/2001 | Schmidt | A61M 15/0086 128/200.23 |
| 7,168,598 B2 * | 1/2007 | Gueret | B65D 1/323 222/548 |
| 7,383,837 B2 * | 6/2008 | Robertson | A61M 15/009 128/200.14 |
| D635,658 S * | 4/2011 | Warby | D24/110 |
| 7,931,175 B2 * | 4/2011 | Hjort | B05C 17/00596 222/567 |
| 2008/0087279 A1 * | 4/2008 | Tieck | A61M 15/0086 128/200.23 |
| 2008/0251551 A1 * | 10/2008 | Huber | A61M 15/009 224/197 |
| 2016/0367770 A1 * | 12/2016 | Matsuda | A61M 15/0086 |

FOREIGN PATENT DOCUMENTS

| | | |
|---|---|---|
| WO | 9220391 A1 | 11/1992 |
| WO | 2005028006 A1 | 3/2005 |

* cited by examiner

INHALER HOUSING

CROSS REFERENCE TO RELATED APPLICATION

This application claims priority to International Application No. PCT/GB2016/053748 filed Nov. 30, 2016, which claims priority to GB 1521241.8, filed Dec. 2, 2015, which are hereby incorporated by reference.

BACKGROUND

Inhalers for medicament delivery are well known and very widely used, especially—but by no means exclusively—in the treatment of asthma and of chronic obstructive pulmonary disease. In a metered-dose type inhaler ("MDI"), a replaceable canister containing the active agent is pressurised with a propellant and is provided with a metering valve which dispenses a controlled dose of the active agent (hereinafter referred to simply as a "dose") each time it is activated. The inhaler canister is carried in a housing which is typically a moulded plastics item which has a body for receiving the canister as an interference fit, and a mouthpiece. The housing is roughly "L" shaped in side view so that the user can place his/her lips around the mouthpiece, which extends roughly horizontally, whilst the housing's body and the inhaler canister are generally upright.

The metering valve is typically activated by manual action on the part of the user. For example the user may be required to press on an exposed end of the canister to slide it a short distance into the body. This action applies pressure to a nozzle end of the canister to activate its metering valve and cause release of a dose. At the same time the user inhales so that the dose is drawn into the lungs along with a volume of air. The housing is open to the exterior to admit this volume of inhaled air. Typically the flow path for the air passes through a space in the housing body around the inhaler canister.

Many users need to carry an inhaler with them routinely. Asthma sufferers, for example, may need to keep an inhaler with them so that they can take a dose in response to an attack. This makes it desirable that the inhaler should be easy and compact to carry. For example some users may wish to be able easily to slip the inhaler into and out of a pocket of their clothing, such as a trouser pocket. The elbowed configuration of a conventional, one-piece moulded, inhaler housing makes the whole unit somewhat cumbersome, awkward to carry about the person and sometimes difficult to slip into a pocket.

Since inhalers are made and sold in large quantities, it is also commercially important to be able to package and transport them in a space-efficient manner. In this respect as well, a one-piece elbowed inhaler housing is less than optimal. Consider for example that if the housing is to be packaged in a cuboidal box, that box must have an increased width to accommodate the laterally protruding mouthpiece.

The prior art includes certain inhalers which are able to be reconfigured for carrying/storage.

U.S. Pat. No. 4,641,644—Andersson et al.—discloses a pocket-size aerosol inhalation device which has a dosage dispensing position and a storage position. The device's mouthpiece is formed by a two-part telescoping deceleration chamber. A socket is provided to receive the inhaler canister. The socket is connected pivotally to an inner part of the telescoping deceleration chamber. In the storage position, the socket is telescopically inserted into an inner part of the deceleration chamber, and the two parts of that chamber are also telescopically collapsed. Disadvantages of this construction include its complexity and the fact that because three different telescoping components must be received one inside another, around the inhaler canister, the lateral dimensions of the collapsed device are unavoidably increased, which does not help in providing a slim and compact device which can easily be slipped into a pocket.

DE3911985—Boehringer Ingelheim KG—discloses an inhaler having a mouthpiece and a cartridge housing which are coupled to one another through a snap fitting which allows one to be rotated relative to the other about an inclined axis. In this way the mouthpiece and the cartridge housing are able to be aligned with one another in one configuration and to form an elbowed or "L" shape in another configuration. No mechanism appears to be provided for positively locating the two parts in the two configurations, however.

U.S. Pat. No. 4,637,528—Wachinski et al.—discloses an aerosol medicament dispenser in which a cylindrical housing for receiving an aerosol container is coupled to a sleeve provided with a mouthpiece through a sliding and pivoting joint. The sleeve is telescopically mounted by engagement of a pair of pin-like projections on a pair of ears formed on the sleeve with slots in opposite side walls of the housing. The sleeve can thus be telescoped into the housing but when drawn out of it can be pivoted to form an "L" shape. The arrangement appears relatively complex and vulnerable to damage or malfunction, which is of course a vital concern since users' health may depend on timely treatment.

WO92/20391—Abbott Laboratories—is somewhat similar to U.S. Pat. No. 4,637,528 in disclosing an inhalation device having a sliding and pivoting joint to couple its two main parts, and similar comments apply.

A need exists for an inhaler housing which can be quickly and easily reconfigured for (a) use and (b) carrying/storage, and which makes it immediately clear to the user whether it is correctly configured for use.

BRIEF DESCRIPTION OF THE DRAWINGS

Specific embodiments of the present invention will now be described, by way of example only, with reference to the accompanying drawings, in which.

DETAILED DESCRIPTION

The present invention relates to inhalers of the type used to deliver an active agent to the lungs of a patient. More specifically it concerns a housing for an inhaler which provides a mouthpiece and a body for receiving an aerosol canister and which is able to be changed by the user between two or more configurations, in one of which the inhaler housing is convenient to carry and store and in one of which the inhaler housing is ready for use.

According to the present invention there is an inhaler housing having a body for receiving an inhaler canister and a mouthpiece which is to be placed in the mouth of a user and through which a dose of an active agent from the inhaler canister is to be delivered, wherein the body and the mouthpiece are rotatably coupled to one another so that by turning the mouthpiece relative to the body the inhaler housing is reversibly converted between a carry configuration in which the mouthpiece and body are mutually aligned, and a use configuration in which the mouthpiece projects laterally from the body, the inhaler housing having a member which is variably elastically deformed as the mouthpiece is turned relative to the body, investing the member with elastic potential energy which varies with the mouthpiece's rotational position with respect to the body and which has at least two minima corresponding to the carry configuration and the use configuration respectively, so that rotation of the mouthpiece relative to the body tends to stop when either of these configurations is reached.

This inhaler housing can be converted quickly and easily by the user between the use and carry configurations, and gives positive visual and haptic indications to the user when the housing is properly configured for use. It is also able to maintain itself stably in either configuration.

The invention is well suited to implementation with a mini inhaler, e.g. roughly the size of a lady's lipstick, using a smaller inhaler canister than the norm.

FIRST EMBODIMENT

Figure 7:
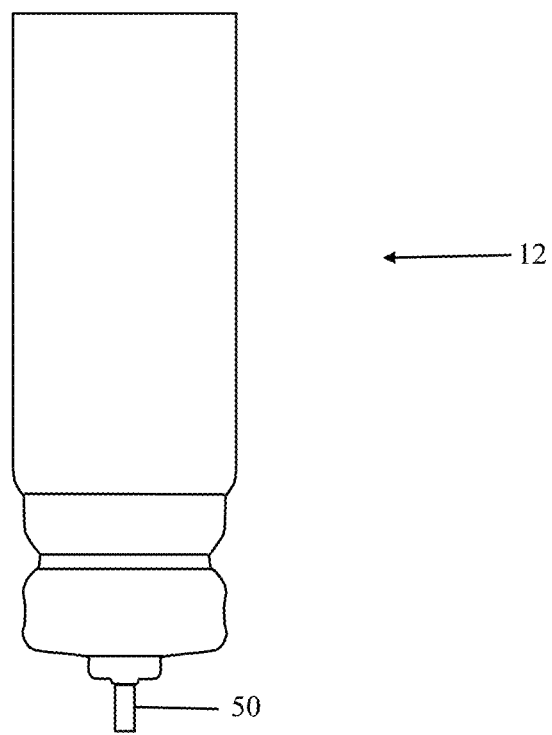
FIG. 7 is a side view of an inhaler canister belonging to the prior art.

The embodiment of the invention depicted in FIGS. 1 to 4 is an inhaler housing 10 which performs several functions:
  it receives and serves to mount an inhaler canister 12 (which is included in FIG. 1b and depicted in more detail in FIG. 7, but omitted from the other drawings);
  it provides for actuation of a metering valve carried by the inhaler canister 12 to dispense a dose;
  it directs the dose through a nozzle arrangement which deflects its direction of travel and outputs it into a mouthpiece 14;
  it provides a route for flow of inhaled air through the mouthpiece, so that the dose can be drawn—along with the inhaled air—into a user's lungs.

In addition, in accordance with the invention, the inhaler housing 10 is constructed such that it can be manually converted between two different configurations. In the configuration depicted in FIGS. 1a and 1b the inhaler housing 10 is roughly "L" shaped in side view. A body 16 which receives the inhaler canister 12 is upright whilst the mouthpiece 14 projects laterally from it. In this configuration the inhaler housing 10 is ready to deliver a dose to the user, so this will be referred to as the "use configuration". In the configuration depicted in FIG. 2 the mouthpiece 14 is aligned with the body 16. The inhaler housing 10 is not to be used to deliver a dose in this state but it does form a roughly linear, cuboidal shape which is more convenient to carry and store, so this will be referred to for brevity as the "carry position".

Figure 1A:
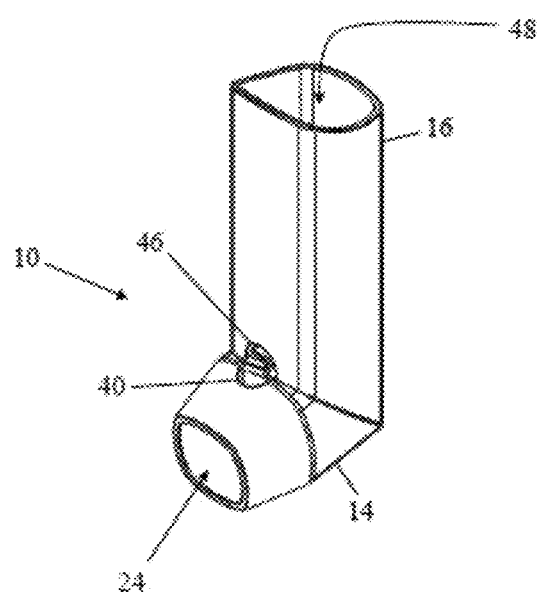
FIG. 1a is a perspective view of an inhaler housing according to a first embodiment of the present invention in a use configuration.
Figure 1C:
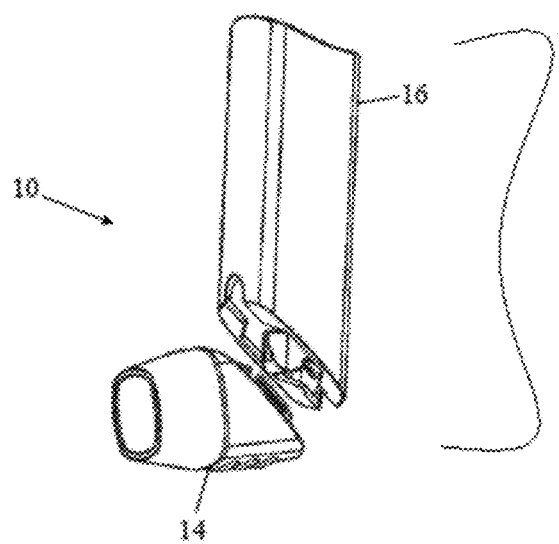
FIG. 1c is a perspective view of the FIG. 1 inhaler housing in a disassembled state.
Figure 1B:
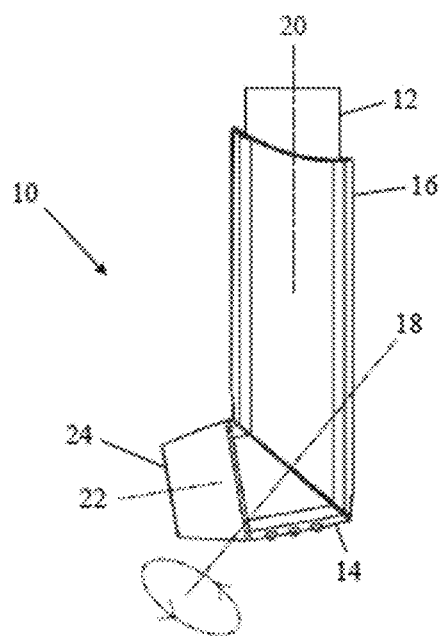
FIG. 1b is a side view of the FIG. 1 inhaler housing in the use configuration. This drawing also shows an inhaler canister.
Figure 1D:
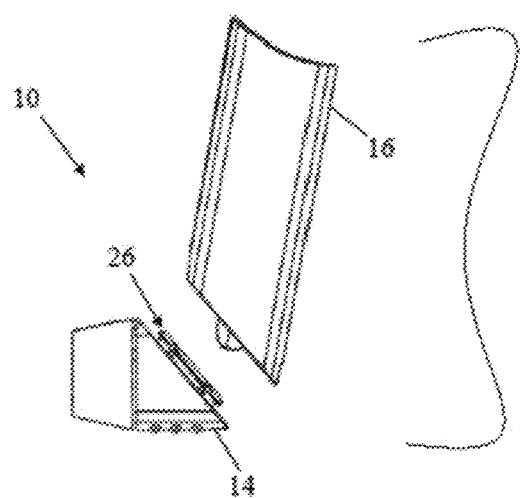
FIG. 1d is a side view of the FIG. 1 inhaler housing in the disassembled state.

As the exploded views—FIGS. 1c and 1d—make clear, the mouthpiece 14 and the body 16 are separate components. In the present embodiment each is a unitary plastics item and may be formed by injection moulding, or by any other suitable moulding or other manufacturing process.

The mouthpiece 14 is pivotally coupled to the body 16. To change the inhaler housing 10 from the use configuration to the carry configuration, the user rotates the mouthpiece 14 through a predetermined angle relative to the body 16. In the present embodiment the predetermined angle is 180 degrees.

Figure 2A:
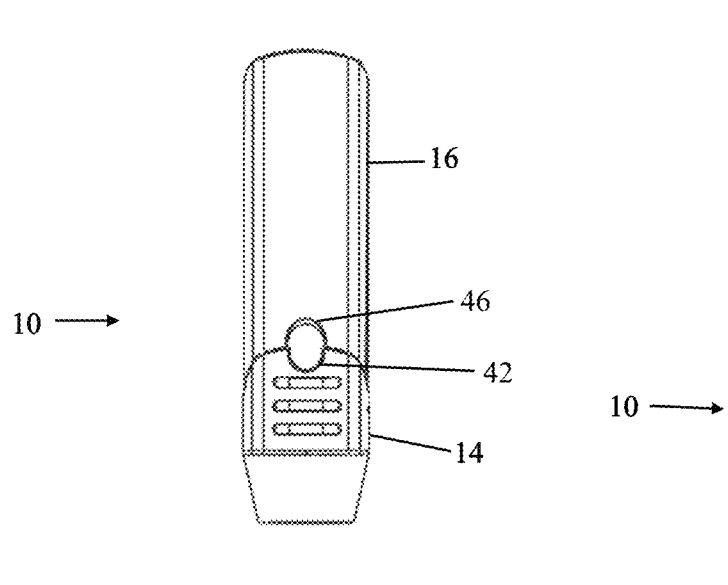
FIG. 2a is a front view of the FIG. 1 inhaler housing in a carry configuration.
Figure 2B:
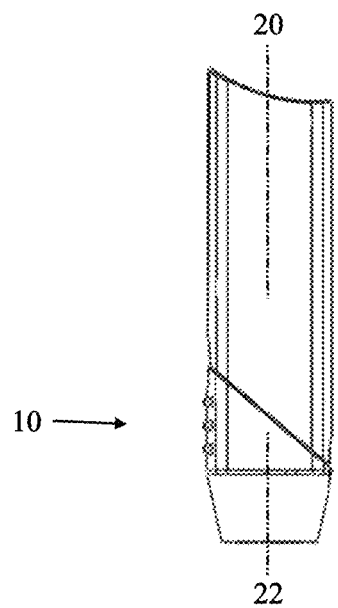
FIG. 2b is a side view of the FIG. 1 inhaler housing in the carry configuration.
Figure 2C:
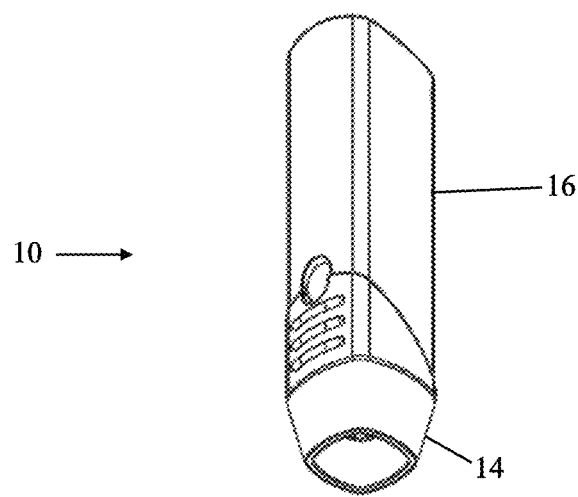
FIG. 2c is a perspective view of the FIG. 1 inhaler in the carry configuration.

In FIG. 1b the axis about which the mouthpiece turns is represented by dashed line 18. This axis is inclined to both the mouthpiece 14 and the body 16. To put this more specifically, one can consider axis of symmetry 20 of the inhaler canister 12 to define a longitudinal axis of the body 16. The rotational axis 18 is inclined to the body's longitudinal axis 20. One can also consider the mouthpiece to have a longitudinal axis 22 perpendicular to its end face 24. The rotational axis 18 is inclined to the mouthpiece's longitudinal axis 22. The result of the inclination of the rotational axis 18 is that turning the mouthpiece transforms the inhaler housing 10 from the generally linear carry configuration, in which the aforementioned longitudinal axes are parallel, as seen in FIG. 2b, to the use configuration, in which the longitudinal axes are angled. The internal angle between the body 16 and the mouthpiece 14 in the use configuration is a little more than 90 degrees, in the present embodiment, so that when the mouthpiece 14 is placed in the user's mouth the body 16 is angled slightly away from the user's face, which is found to be convenient.

The pivotal coupling between the mouthpiece 14 and the body 16 is formed in such a way as to define at least two stable positions. Stable positions are not necessarily end points of the rotational travel of the mouthpiece, but are points in this rotational travel at which the rotation naturally tends to stop. The parts will not turn in either direction, from a stable position, without an applied torque.

The pivotal coupling is formed in such a manner that at least one part of it is elastically deformed during rotation. The degree of deformation varies with rotational position. So turning the mouthpiece 14 relative to the body 16 causes the pivotal coupling to be invested with elastic potential energy. This elastic potential energy is a function of rotational position—i.e. of the rotational angle of the mouthpiece 14 with respect to the body 16. This function has minima at the angles corresponding to the stable positions.

Hence in order to move away from a stable position in either rotational direction, a torque must be exerted, doing mechanical work to deform the pivotal coupling and increase its potential energy.

The pivotal coupling has a first stable position corresponding to the use configuration and a second stable position corresponding to the carry configuration. In the present embodiment it also has four further stable positions. The stable positions are at regular angular intervals of—in this case—60 degrees.

The pivotal coupling is formed by engagement of male features of the mouthpiece 14 with female features of the body 16 in the present embodiment, although this could be reversed—that is, the male features could be provided on the body 16 and the female features on the mouthpiece 14.

Figure 3A:
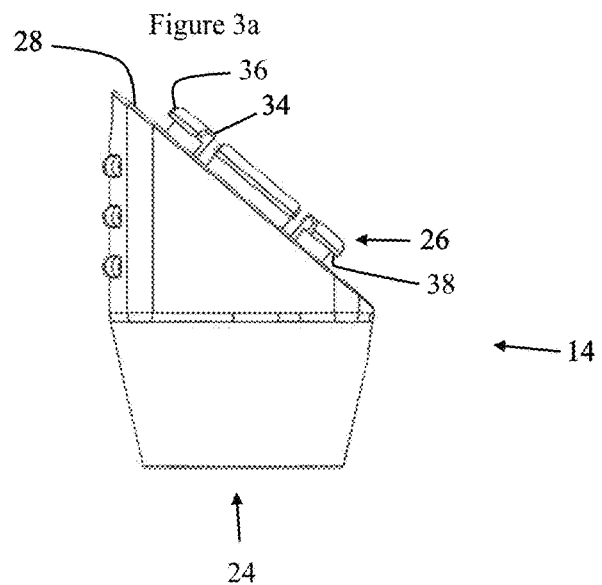
FIG. 3a shows a mouthpiece of the FIG. 1 inhaler housing in side view.
Figure 3B:
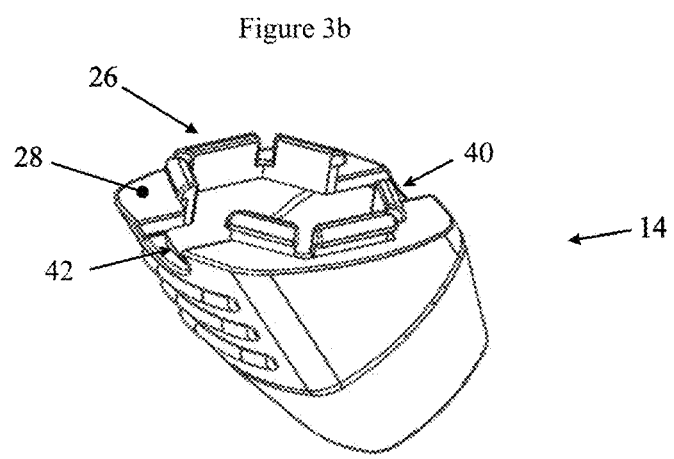
FIG. 3b shows the mouthpiece of the FIG. 1 inhaler housing in perspective from one side and above.

Looking in particular at FIG. 3, the male features comprise a set of lugs 26 upstanding from a first abutment face 28. The female features—best seen in FIG. 4—comprise an opening 30 in a second abutment face 32 into which the lugs 26 are inserted. A snap fit is thereby formed—the mating features are somewhat stressed during insertion and then snap back to lock together. In FIG. 3a it can be seen that each of the lugs 26 has a head 34 which is shaped for this purpose, having an inclined ramp surface 36 leading to an undercut shoulder 38. As the lugs 26 are pushed into the opening 30 the ramp surfaces 36 first engage with the periphery of the opening 30 and due to their inclination they cause the lugs 26 to be elastically deformed inwardly, toward one another, until a point is reached where the heads 34 have passed through the opening, enabling the lugs to snap outwards to bring their shoulders into engagement with the rear periphery of the opening 30, locking the components together.

The first and second abutment faces 28, 32 are thereby brought into contact with one another. In the present embodiment these faces are flat. They move over one another as the mouthpiece 14 is turned. It is the abutment faces 28, 32 that define the inclination of the rotational axis 18 shown in FIG. 1b. The first abutment face 28 of the mouthpiece 14 is inclined to the axis 22 of that part. The second abutment face 32 of the body 16 is inclined to the axis 20 of that part.

Figure 3C:
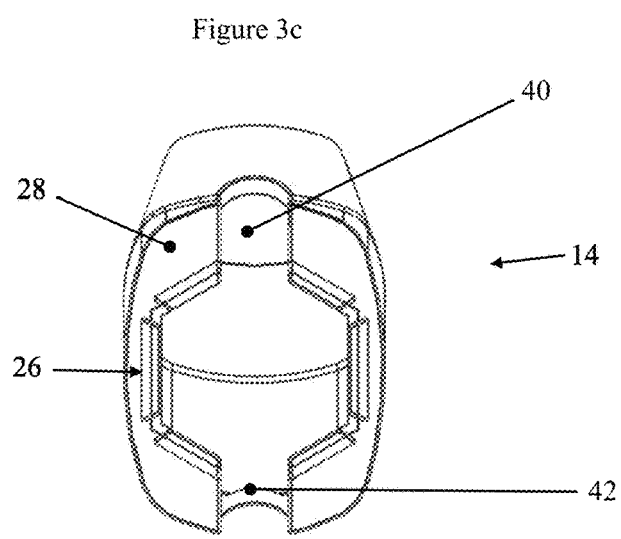
FIG. 3c shows the mouthpiece of the FIG. 1 inhaler housing from above.

Viewed in plan, as in FIG. 3c, the male features of the mouthpiece 14 have a polygonal arrangement. More specifically, in the present embodiment the lugs 26 have a substantially hexagonal arrangement. Each lug 26 forms one edge of this hexagon, although each lug is separated from its neighbour so that the lugs 26 are able to deform independently of one another. Also the hexagonal arrangement is interrupted by first and second mouthpiece flow passages 40, 42 whose function will be described below.

Figure 4A:
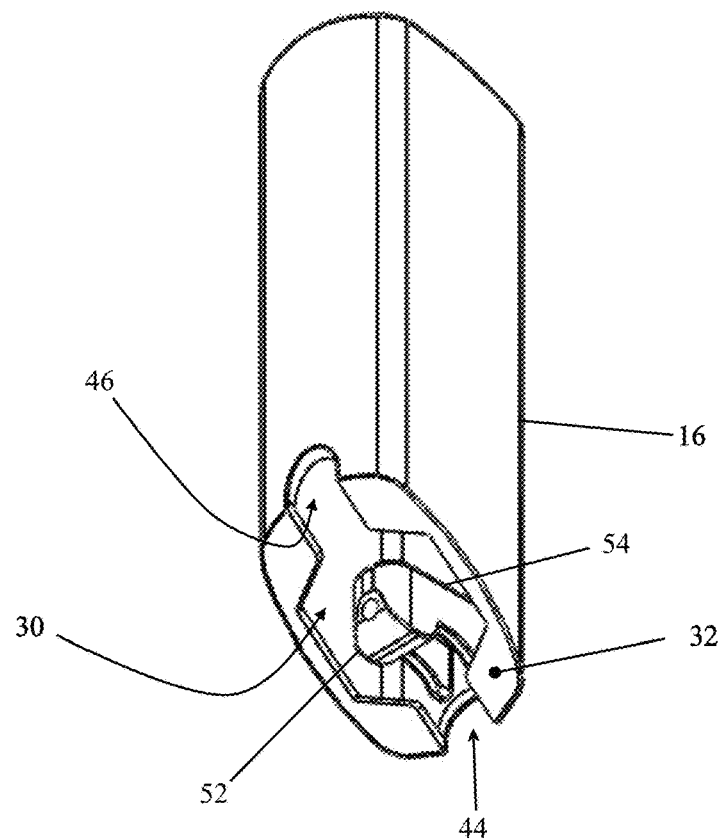
FIG. 4a shows a body of the FIG. 1 inhaler in perspective.
Figure 4B:
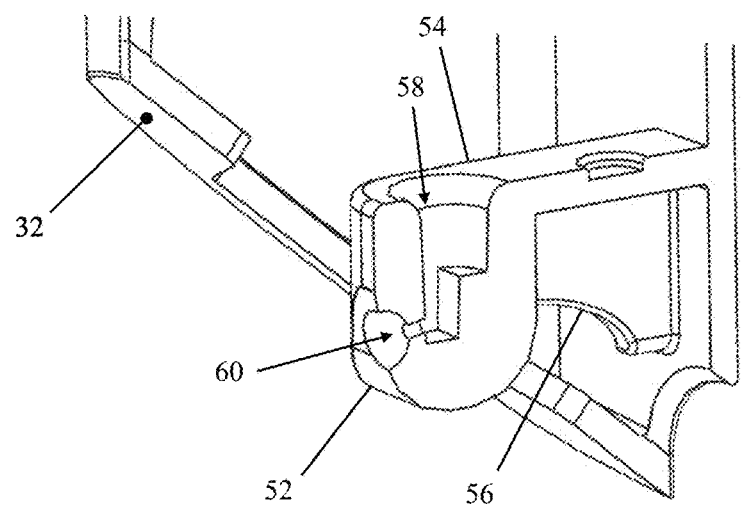
FIG. 4b is an enlarged view of part of the body of the FIG. 2 inhaler, a front portion of which is omitted to reveal internal detail.

In FIG. 4a it can be seen that the opening 30 is shaped complementarily to the arrangement of the lugs 26, being substantially hexagonal although it too is interrupted by first and second body flow passages 44, 46.

Figure 8:
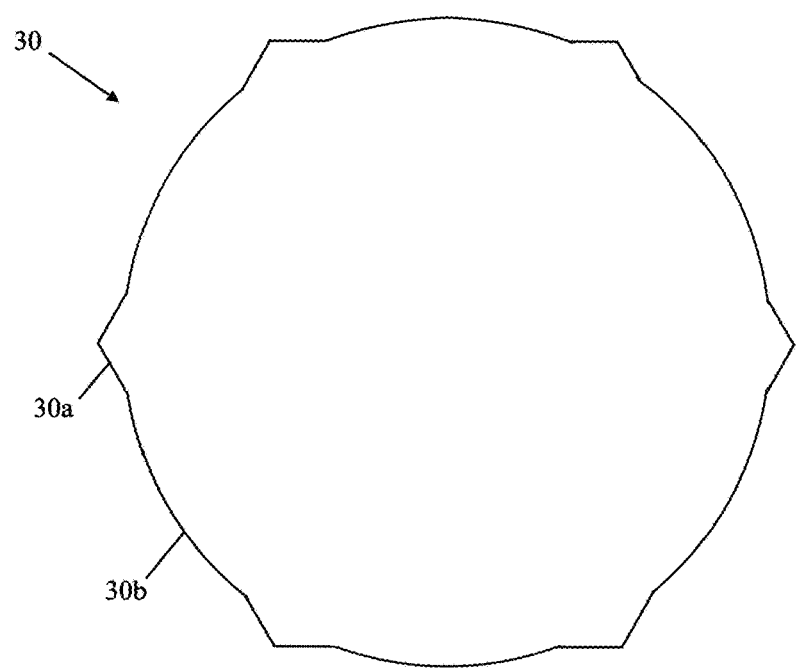
FIG. 8 is a plan view of an alternative shape for an opening through which parts of the inhaler engage.

An alternative polygonal shape for the opening 30 is represented in FIG. 8. This is a modified polygonal shape—more specifically a modified hexagon. The shape is constructed by overlaying a circle upon the hexagon, so that vertex portions 30a of the hexagon are joined by intermediate portions 30b lying on a circular locus. The effect is that the lugs 26 are able to expand into the vertex portions 30a, but at intermediate rotational positions a secure engagement is maintained between the lugs and the periphery of the opening 30, since the shoulders 38 remain in engagement throughout their entire length.

Figure 9:
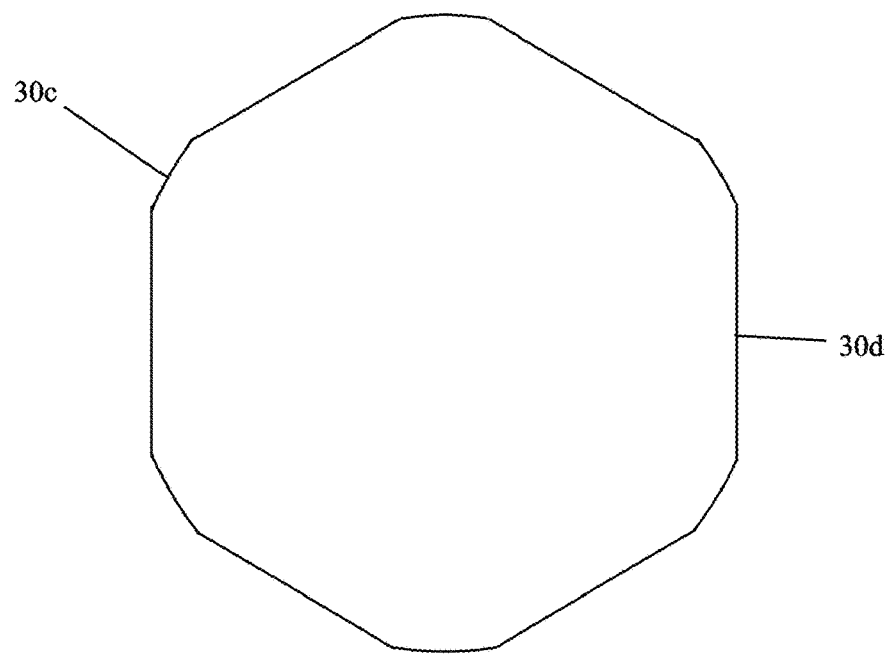
FIG. 9 is a plan view of a further alternative shape through which parts of the inhaler engage.

A further alternative polygonal shape for the opening 30 is represented in FIG. 9 and is again formed by overlaying a circle upon a polygon (specifically a hexagon). In this case part-circular fillets 30c lying on the said circle are provided at each vertex of the hexagon formed by straight sides 30d. The effect of the fillets is to ensure that the ends of shoulders 38 overhang and engage with the periphery of the opening 30 at all points in their rotation, and any tendency for these ends to disengage as they pass the vertices of the hexagon is avoided.

In the aforementioned stable rotational positions of the mouthpiece 14 relative to the body 16, the lugs 26 are each aligned parallel to, and lie alongside, a respective edge of the hexagonal opening 30. It will be apparent that the hexagonal arrangement of the male and female features creates six such stable positions. As the user turns the mouthpiece, moving it away from a stable position, these features—especially but not necessarily exclusively the lugs 26—must be deformed somewhat. The lugs 26 are bent inwards progressively as the mouthpiece 14 is turned, stressing them and investing them with elastic potential energy. As the mouthpiece approaches the next stable position the lugs start to move outward, toward their un-stressed positions, so that their potential energy is released—or is at least at a minimum—when the next stable position is reached. The result is that in order to turn the mouthpiece in either direction from a stable position, the user has to exert a torque above that needed merely to overcome friction. As the mouthpiece turns it naturally tends to stop in the stable positions and a haptic signal is given to the user—due to a variation of reaction torque—as the mouthpiece is moved through the stable positions. If released in a position between two stable positions, the mouthpiece may of its own accord move to the nearest of them.

Due to the hexagonal arrangement of the male and female features, moving from the carry configuration to the use configuration involves passing through two intermediate stable positions. If the position of the mouthpiece in the carry configuration is taken to be at zero degrees and its position in the use configuration is at 180 degrees then the intermediate stable positions are at 60 and 120 degrees. This is not problematic—the used will clearly be able to see, at either of these positions, that the inhaler housing 10 is not suitably configured for use.

The depicted formation of the lugs 26, in combination with a suitable choice of resilient polymer material, ensures that they continue to function despite prolonged and repeated use. Also because the lugs 26 move independently of one another the failure of one or more lugs can be accommodated without failure of the device as a whole.

The arrangement of the male and female features need not be hexagonal. It could instead have the form of another polygon. Preferably this is a polygon with an even number of sides, so that stable positions corresponding to the use and carry configurations can be spaced 180 degrees apart. An octagonal arrangement may for example be used, or a square arrangement.

The present embodiment has no end stops for the rotational travel of the mouthpiece 14 relative to the body 16. The mouthpiece can be turned through a full 360 degrees and beyond.

Looking now at the detail of the body 16, this is an elongate part which is hollow, forming an open-ended chamber 48 (see FIG. 1a) for receiving the inhaler canister 12. The length of the body 16 is such that the inhaler canister 12 projects from its open end, as seen in FIG. 1b. The canister forms a sliding fit in the body 16 and can thus be depressed by the user. The inhaler canister 12 has an outlet tube 50 (see FIG. 7) depression of which actuates its metering valve (not shown) to cause release of a dose through it.

Within the body 16 and integrally formed with it is a nozzle element 52 (see FIGS. 4a and 4b) carried on arms 54 reinforced by fillets 56. A delivery passage is formed through the nozzle element 52 and is elbowed to provide an upwardly open inlet 58 into which the outlet tube 50 of the canister is inserted, in use, and a laterally directed delivery nozzle 60 which through which the dose is dispensed into the mouthpiece 14, in use. The form of the delivery nozzle 60 is chosen to provide a desired spray pattern, and is in the illustrated example an outwardly divergent frustum of a cone. When the inhaler canister 12 is depressed by the user, it is the nozzle element 52 that reacts the force applied to the canister and so actuates the metering valve.

The mouthpiece 14 (see FIG. 3 in particular) is a hollow item, thus forming a chamber into which the dose is delivered and from which it is drawn by the action of the user's lungs through its open end 24. The mouthpiece seen in the drawings provides quite a short distance to be traversed by the dose, but it could be longer to form what is referred to as a delay chamber. The first abutment face 28 has an opening 64, formed within the male features of the pivotal coupling, through which the interior of the mouthpiece 14 communicates with the interior of the body 16, to receive the dose.

When the inhaler housing 10 is in the use configuration the first mouthpiece flow passage 40 is aligned with the first body flow passage 44 and the second mouthpiece flow passage 42 is aligned with the second body flow passage 46. The passages are visible at the exterior of the inhaler housing and their alignment—or, in the intermediate stable positions, their non-alignment—gives the user a visual indication of whether the mouthpiece 14 has been turned all the way to its use position.

Figure 5A:
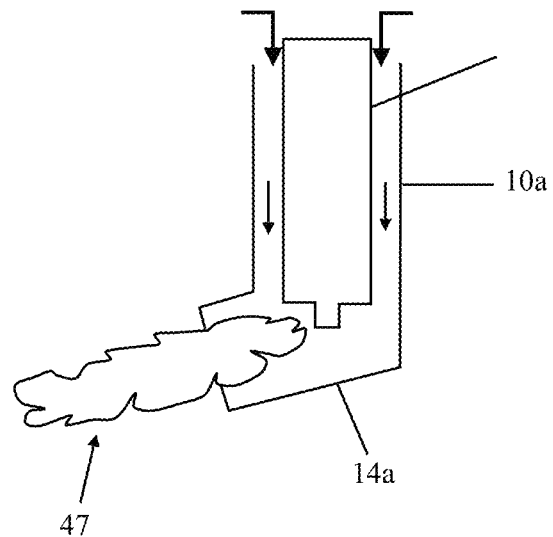
FIG. 5a is a stylised cross-sectional view of a prior art inhaler containing arrows to indicate air flow in use.

In the use configuration the passages 40, 44 and 42, 46 provide respective routes for entry of inhaled air to the inhaler housing 10. Refer in this regard to FIG. 5. FIG. 5a shows the pattern of air flow in a prior art inhaler device. The air enters housing 10a through its open upper end and flows through a space around the inhaler canister 12a to reach the mouthpiece 14a where it carries with it the dose 47.

Figure 5B:
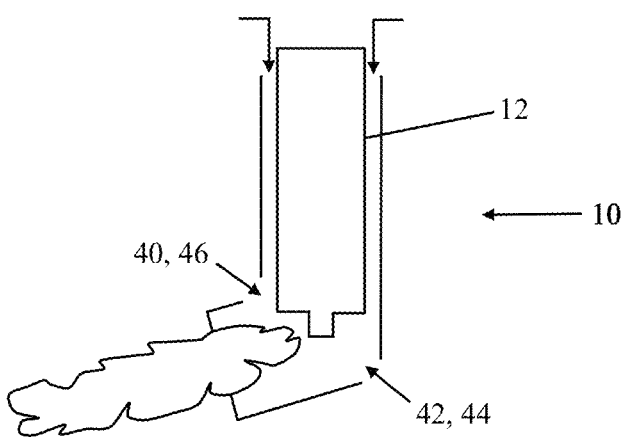
FIG. 5b is a similarly stylised view of an inhaler embodying an aspect of the present invention, again with arrows to indicate air flow.

Compare this with FIG. 5b, representing air flow in an embodiment of the present invention. Here again air can flow through the space around the canister 12, but additional air enters the inhaler housing 10 through the flow passages 40, 46 and 42, 44. One advantageous effect is that the space around the canister 12 can be reduced, without unduly impeding air flow, because additional routes are provided to admit the air. Hence the lateral dimensions of the inhaler housing 10 can correspondingly be reduced, making for a more compact and convenient package.

SECOND EMBODIMENT

Figure 6:
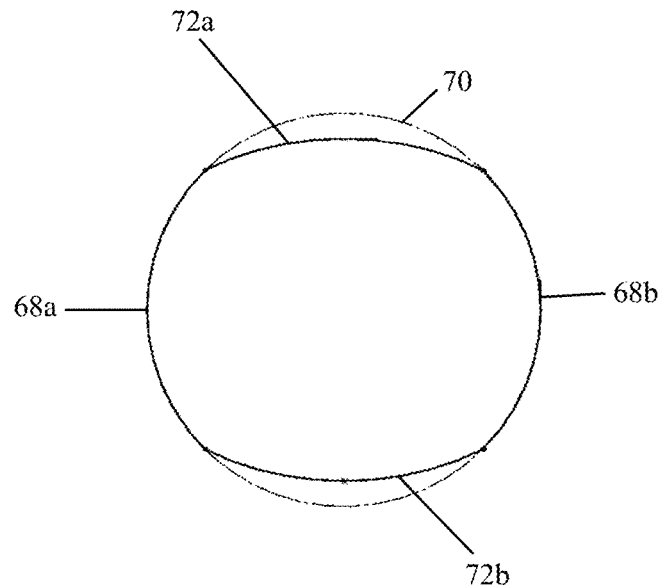
FIG. 6 is a simplified representation of coupling features in an inhaler housing according to a second embodiment of the present invention.

The male and female features forming the pivotal coupling between the mouthpiece 14 and the body 16 may be formed to have only two stable positions, corresponding respectively to the use and carry configurations. To this end these features may have an oval or quasi-oval or elliptical plan shape. FIG. 6 shows a suitable shape. In a second embodiment of the invention, both (a) the opening 30 in the second abutment face 32 and (b) the lugs 26 form this shape, when viewed in plan. The shape has opposed end regions 68a, 68b lying on a circle 70, the end regions being connected by opposed flank regions 72a, 72b which lie within the circle 70. The flank regions are outwardly convex but have a larger radius of curvature than the circle 70. Note that in the drawing it is the solid lines that show the shape in question. The dotted lines indicate the notional circle 70 on which the end regions lie.

The precise form of the shape in question may differ in other embodiments. But it provides only two positions in which the male and female parts can engage without deformation, and these are 180 degrees apart.

What is claimed is:

1. An inhaler housing, comprising:
   a body configured to receive an inhaler canister; and
   a mouthpiece configured to be placed in the mouth of a user and through which a dose of an active agent from the inhaler canister is to be delivered,
   wherein the body and the mouthpiece are rotatably coupled to one another so that by turning the mouthpiece relative to the body the inhaler housing is reversibly converted between a carry configuration in which the mouthpiece and body are mutually aligned, and a use configuration in which the mouthpiece projects laterally from the body, the inhaler housing having a member which is variably elastically deformed as the mouthpiece is turned relative to the body, investing the member with elastic potential energy which varies with the mouthpiece's rotational position with respect to the body and which has at least two minima corresponding to the carry configuration and the use configuration respectively, so that rotation of the mouthpiece relative to the body results in a stable position when either of these configurations is reached, and wherein the rotatable coupling of the body to the mouthpiece has no fixed end stop so that the mouthpiece is able to rotate through 360 degrees and beyond relative to the body.

2. An inhaler housing as claimed in claim 1 in which the mouthpiece and the body are rotatably coupled through at least one male engagement part on one of the mouthpiece and the body received by at least one female engagement feature on the other of the mouthpiece and the body.

3. An inhaler housing as claimed in claim 2 in which the aforementioned member which is variably elastically deformed comprises the at least one male engagement part.

4. An inhaler housing as claimed in claim 2 in which the rotatable coupling of the body to the mouthpiece has an axis and in which the at least one male engagement part and the at least one female engagement feature, viewed in a direction along the axis, form complementary non-circular shapes.

5. An inhaler housing as claimed in claim 4 in which the at least one male engagement part and the at least one female engagement feature, viewed along the axis, form complementary polygonal shapes.

6. An inhaler housing as claimed in claim 2 in which the rotatable coupling of the body of the mouthpiece has an axis and in which at least one of (a) the at least one male engagement part and (b) the at least one female engagement feature, viewed in a direction along the axis, form a polygonal shape.

7. An inhaler housing as claimed in claim 6 in which the polygonal shape has an even number of sides.

8. An inhaler housing as claimed in claim 6 in which the polygonal shape is a hexagon or an octagon.

9. An inhaler housing as claimed in claim 2 in which the rotatable coupling of the body to the mouthpiece has an axis and in which at least one of (a) the at least one male engagement part and (b) the at least one female engagement feature, viewed in a direction along the axis, forms a shape which is oval or elliptical, so that the elastic potential energy has minima at only two rotational positions of the mouthpiece with respect to the body.

10. An inhaler housing as claimed in claim 2 in which the at least one male engagement part comprises a lug with an undercut head and the at least one female engagement feature comprises an opening to receive the lug such that its undercut head snaps into place to couple the mouthpiece to the body.

11. An inhaler housing as claimed in claim 1 in which the rotatable coupling of the body to the mouthpiece has an axis which is inclined with respect to both the mouthpiece and the body.

12. An inhaler housing as claimed in claim 1 in which the body and the mouthpiece have respective ends which are in mutual abutment, each of the said ends being cut away to form a part flow passage, the part flow passages of the body and the mouthpiece being arranged to be aligned when the inhaler housing is in the use configuration to provide a route for entry of air to the housing and a visual confirmation that the housing has been properly configured for use.

* * * * *